(12) United States Patent
Lane et al.

(10) Patent No.: US 9,833,154 B2
(45) Date of Patent: *Dec. 5, 2017

(54) SUPRASYSTOLIC MEASUREMENT IN A FAST BLOOD-PRESSURE CYCLE

(71) Applicant: Welch Allyn, Inc., Skaneateles Falls, NY (US)

(72) Inventors: John A. Lane, Weedsport, NY (US); David E. Quinn, Auburn, NY (US); Matthew J. Kinsley, Liverpool, NY (US); Tyson B. Whitaker, Arden, NC (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 635 days.

This patent is subject to a terminal disclaimer.

(21) Appl. No.: 14/466,356

(22) Filed: Aug. 22, 2014

(65) Prior Publication Data
US 2014/0364748 A1 Dec. 11, 2014

Related U.S. Application Data

(63) Continuation of application No. 12/650,984, filed on Dec. 31, 2009, now Pat. No. 8,840,561.

(51) Int. Cl.
*A61B 5/00* (2006.01)
*A61B 5/0225* (2006.01)
*A61B 5/022* (2006.01)

(52) U.S. Cl.
CPC ........ *A61B 5/0225* (2013.01); *A61B 5/02225* (2013.01); *A61B 2562/0219* (2013.01); *Y10T 29/49826* (2015.01)

(58) Field of Classification Search
None
See application file for complete search history.

(56) References Cited

U.S. PATENT DOCUMENTS

| 5,653,241 A | 8/1997 | Harada et al. |
| 6,331,159 B1 | 12/2001 | Amano et al. |
| 6,712,768 B2 | 3/2004 | Ogura et al. |

(Continued)

OTHER PUBLICATIONS

International Patent Application No. PCT/US2010/060382: International Search Report and Written Opinion; dated Feb. 28, 2011.

(Continued)

*Primary Examiner* — Patricia Mallari
*Assistant Examiner* — Sarah Kingsley
(74) *Attorney, Agent, or Firm* — Finnegan, Henderson, Farabow, Garrett & Dunner LLP

(57) ABSTRACT

Disclosed herein is a system for monitoring a patient that includes a cuff configured to inflate to at least partially occlude an artery of the patient and a cuff controller configured to inflate the cuff during a dynamic phase and generally maintain inflation of the cuff at about a target pressure during a static phase. The system also includes a sensor configured to receive a signal associated with the at least partially occluded artery and generate an output signal based on the received signal, and a cuff control module configured to determine the target pressure during the dynamic phase and based on the output signal, and control the cuff controller during the dynamic phase and the static phase.

21 Claims, 4 Drawing Sheets

(56) References Cited

U.S. PATENT DOCUMENTS

| | | |
|---|---|---|
| 6,793,628 B2 | 9/2004 | Ogura et al. |
| 6,976,966 B2 | 12/2005 | Narimatsu |
| 6,994,675 B2 | 2/2006 | Sharrock |
| 7,153,269 B1 * | 12/2006 | Blansett ................. A61B 5/022 600/490 |
| 7,468,037 B2 | 12/2008 | Illyes et al. |
| 8,840,561 B2 * | 9/2014 | Lane ................. A61B 5/02225 600/495 |
| 2004/0077959 A1 | 4/2004 | Narimatsu |
| 2006/0200027 A1 | 9/2006 | Evans |
| 2006/0224070 A1 | 10/2006 | Sharrock et al. |
| 2007/0185401 A1 * | 8/2007 | Quinn ................. A61B 5/0225 600/485 |
| 2009/0012411 A1 | 1/2009 | Lowe et al. |
| 2009/0287097 A1 | 11/2009 | Lowe |

OTHER PUBLICATIONS

McLaughlin, J. et al. Piezoelectric sensor determination of arterial pulse wave velocity: Physiol. Meas. 24:693-702 (2003).

Alpert, B.S. "Clinical evaluation of Welch Allyn SureBP algorithm for automated blood pressure measurement" Blood Pressure Monitoring 12(4):215-218 (2007).

* cited by examiner

SUPRASYSTOLIC MEASUREMENT IN A FAST BLOOD-PRESSURE CYCLE

CROSS-REFERENCE TO RELATED APPLICATIONS

The present application is a continuation of and claims priority to U.S. Non-Provisional application Ser. No. 12/650,984, now U.S. Pat. No. 8,840,561, filed on Dec. 31, 2009, and titled "Suprasystolic Measurement in a Fast Blood-Pressure Cycle", which is hereby incorporated by reference in its entirety.

TECHNICAL FIELD

This application is directed to systems and methods for monitoring a patient, and in particular, to a suprasystolic measurement in a fast blood-pressure cycle.

BACKGROUND

Traditional non-invasive blood pressure monitoring devices operate by inflating a cuff to a pressure well above a patient's systolic blood pressure. Because the systolic pressure is usually not know prior to inflation, the cuff must be inflated to such a high pressure to ensure that the patient's arterial blood flow is completely occluded. Once well above systole, the cuff is deflated and the systolic and diastolic pressures are calculated based on signals provided during cuff deflation.

Some methods have been developed to estimate blood pressures during cuff inflation. These methods, however, are generally inaccurate and/or slow. Consequently, such methods cannot provide a commercially useful determination of systolic pressure that must meet certain regulatory standards.

More recently, a suprasystolic measurement technique has been developed, as described by U.S. Pat. No. 6,994,675. This technique includes inflating a cuff to a "suprasystolic pressure," about 10-40 mmHg above a patient's systolic pressure. Suprasystolic pressure can be maintained while signals from the occluded artery are collected. These signals are processed to determine a number of hemodynamic parameters, such as, for example, aortic compliance.

Current suprasystolic methods require determining a patient's systolic blood pressure prior to inflating the cuff because the suprasystolic pressure is directly proportional to the systolic pressure. As described above, current methods for accurately determining systolic pressure rely on inflating and then deflating a cuff. Thereafter, the cuff is re-inflated to a suprasystolic pressure (i.e., about 10-40 mmHg above systole). Such repeated inflation and deflation of the cuff takes additional time and exposes the patient to the additional discomfort.

The present disclosure is directed to systems and methods for providing a suprasystolic measurement in less time and with less patient discomfort than prior techniques. In one exemplary embodiment, a patient's systolic pressure can be determined during cuff inflation. Following inflation, the cuff can be maintained at a suprasystolic pressure determined by the systolic pressure. During this suprasystolic phase, signals from the patient can be measured and analyzed to determine one or more hemodynamic parameters. Thus, data obtained during an inflationary, or dynamic phase, of a pressure cycle may be used in real time to determine if and how a suprasystolic measurement should be conducted. Combining a systolic pressure determination and suprasystolic measurement into a single pressure cycle can reduce cycle time and minimize patient discomfort.

SUMMARY

A first aspect of the present disclosure includes a system for monitoring a patient having a cuff configured to inflate to at least partially occlude an artery of the patient and a cuff controller configured to inflate the cuff and generally maintain inflation of the cuff at about a target pressure. The system also includes a sensor configured to receive a signal associated with the at least partially occluded artery and generate an output signal based on the received signal, and a cuff control module configured to determine the target pressure during the dynamic phase and based on the output signal, and control the cuff controller during the dynamic phase and the static phase.

A second aspect of the present disclosure includes a method of determining a hemodynamic parameter of a patient that includes providing a cuff configured to at least partially occlude a vessel of the patient. The method includes inflating the cuff to a target pressure during a dynamic phase, wherein the target pressure can be determined during the dynamic phase, maintaining the inflatable cuff at about the target pressure during a static phase, and determining the hemodynamic parameter during the static phase.

A third aspect of the present disclosure includes a processor configured to transmit a first signal to inflate a cuff to at least partially occlude an artery of a patient and receive a signal from the cuff representative of vibrations from the at least partially occluded artery. The processor can further determine a target pressure during cuff inflation based on the received signal, and transmit a second signal to generally maintain cuff inflation at about the target pressure.

Additional objects and advantages of the present disclosure will be set forth in part in the description which follows, and in part will be obvious from the description, or may be learned by practice of the present disclosure. The objects and advantages of the present disclosure will be realized and attained by means of the elements and combinations particularly pointed out in the appended claims.

It is to be understood that both the foregoing general description and the following detailed description are exemplary and explanatory only and are not restrictive of the present disclosure, as claimed.

The accompanying drawings, which are incorporated in and constitute a part of this specification, illustrate several embodiments of the present disclosure and together with the description, serve to explain the principles of the present disclosure.

DETAILED DESCRIPTION

Disclosed herein are patient monitoring systems and methods of using such systems. In particular, the present disclosure provides a suprasystolic measurement in a fast blood-pressure cycle. Both blood-pressure determination and suprasystolic measurement are generally completed in less time than a typical blood pressure assessment alone, such as, for example, about 25 seconds. The time is reduced in part because cuff re-inflation can be avoided.

The present disclosure also permits the use of real time data collected during inflation in a subsequent suprasystolic measurement. For example, an accurate suprasystolic pressure can be based on a systolic pressure determined during inflation. Further, if a suprasystolic measurement should occur, the duration of a suprasystolic measurement, or what sort of signal analysis should be performed during suprasystolic measurement can be determined during inflation.

In some embodiments, the combined blood-pressure determination and suprasystolic measurement can provide dynamic information to a decision tree or algorithm to determine a particular hemodynamic parameter. For example, a suprasystolic measurement might be conducted on patients having certain physiological indicators, such as, weight, heart rate, or blood pressure. A patient's physiological indicators may be determined during inflation. If one or more of these indicators fails to meet certain criteria, the suprasystolic measurement could be cancelled and the patient notified. Thus, various indicators could be tested during inflation to ensure suitable suprasystolic measurement.

In yet other embodiments, the present system can permit rapid analysis of hemodynamic data gathered from unloaded, partially loaded, or fully loaded vessels. Before inflation, the patient's vessels are unloaded and blood flow is not restricted. During inflation, termed a "dynamic phase," the patient's vessels are progressively loaded, reducing blood flow. At suprasystolic pressure, the patient's vessels are completely loaded or occluded, termed a "static phase." Data gathered during these different conditions may be compared and contrasted to determine one or more hemodynamic parameters. For example, a beat-to-beat time during the dynamic phase, when the vessel is partially occluded, may be compared with a beat-to-beat time during the static phase, when the vessel is completely occluded. Such data comparison can provide an indication of irregular heart beat timing. Two or more separate conditions could also be used to attenuate signal noise using various de-noising algorithms.

Figure 1:
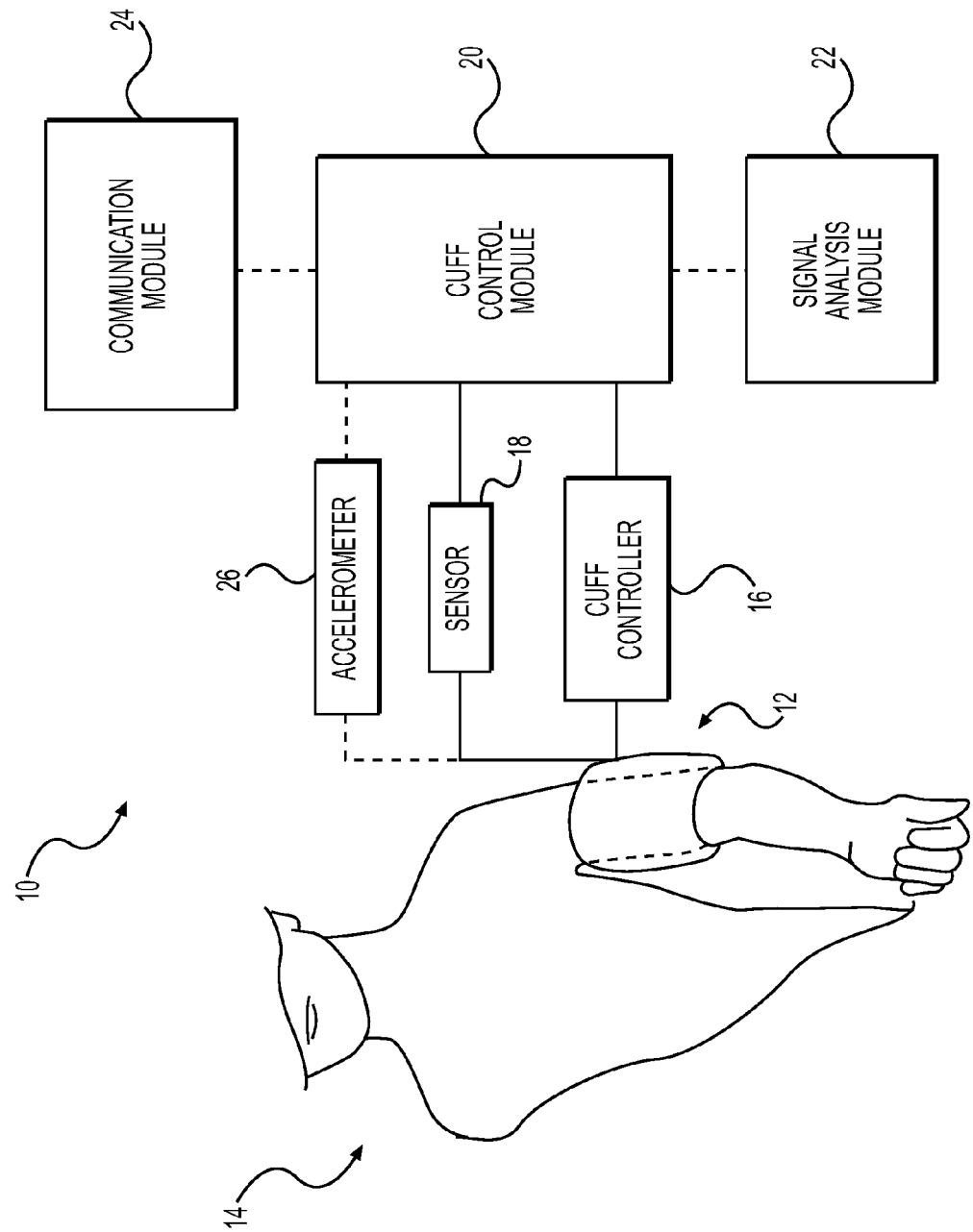
FIG. 1 illustrates a monitoring system, according to an exemplary embodiment.

FIG. 1 illustrates a system 10, according to an exemplary embodiment of the present disclosure. System 10 can be configured to monitor a patient, and in some embodiments, to determine a hemodynamic parameter of the patient.

System 10 can include a cuff 12 configured to at least to partially occlude the movement of blood through a vessel of patient 14. In some embodiments, cuff 12 can be configured to completely completely occlude an artery of patient 14. Although shown in FIG. 1 surrounding the upper arm of patient 14, cuff 12 may be adapted for placement on any suitable part of patient 14, including, for example, a wrist, a finger, an upper thigh, or an ankle. In addition, one or more cuffs 12 could be placed at different locations about patient 14 for use with system 10.

Cuff 12 can include an inflatable device, wherein the pressure or volume within cuff 12 may be controlled by a cuff controller 16 operably associated with cuff 12. Cuff controller 16 can include a pump or similar device to inflate cuff 12. For example, cuff controller 16 could supply cuff 12 with a fluid to increase the pressure or volume of cuff 12. In other embodiments, cuff controller 16 could include mechanical, electrical, or chemical devices configured to control vessel occlusion of patient 14 via cuff 12.

In some embodiments, cuff controller 16 can generally maintain cuff 12 at about a target pressure. For example, once a target pressure has been determined, as explained in detail below, cuff controller 16 could control cuff 12 to provide patient 14 with a generally constant pressure. While the present disclosure refers to a target pressure, it should be understood that the actual pressure applied by cuff 12 may vary. As such, the pressure applied to patient 14 may generally remain within appropriate limits, such as, for example, with 2%, 5%, 10%, or 20% of the target pressure.

System 10 can further include a sensor 18 configured to receive a signal associated with patient 14. In some embodiments, sensor 18 can be configured to receive a signal associated with an at least partially occluded vessel of patient 14. Such an input signal can arise from blood movement through a partially occluded vessel or from a signal associated with an occluded blood vessel. Sensor 18 could sample multiple times at various intervals. In yet other embodiments, sensor 18 could provide an indication of blood vessel movement, such as, for example, oscillations arising from vascular expansion or contraction. For example, sensor 18 could be configured to detect a pressure or volume of cuff 12 that may vary periodically with the cyclic expansion and contraction of an artery of patient 14. In particular, sensor 18 could determine a blood pressure or other hemodynamic parameter associated with patient 14—using an oscillometric method.

In some embodiments, sensor 18 could detect a volume or a pressure associated with cuff 12. For example, sensor 18 could include a pressure sensor and may be located within or about cuff 12. System 10 could further operate with a plurality of sensors 18, and may include a high-resolution sensor or pneumatic sensor designed to operate in conjunction with cuff 12.

Sensor 18 can further be configured to generate an output signal. The output signal may be generated based on an input signal received from patient 14. In one aspect, the output signal can include a representation of an input signal associated with cuff 12 and/or patient 14.

Cuff 12, cuff controller 16, and sensor 18 may be operably associated with a cuff control module 20. Specifically, cuff control module 20 could include one or more processors configured to control one or more operations of cuff 12, cuff controller 16, or sensor 18. For example, cuff control module 20 can control inflation of cuff 12 via control of cuff controller 16.

In some embodiments, cuff control module 20 can calculate a target pressure. This calculation may be based on an output signal from sensor 18, as described above. Cuff control module 20 may also control inflation of cuff 12, inflation of cuff 12 to the target pressure, or generally maintaining inflation of cuff 12 at about the target pressure.

In operation, cuff control module 20 could calculate a target pressure during inflation of cuff 12. Such a calculation could take less than about 15 seconds. Cuff control module 20 could then generally maintain cuff 12 at about the target pressure for a defined time period, such as, for example, less than about 10 seconds. In other embodiments, the target pressure could be generally maintained for a defined number of cardiac cycles, such as, for example, six, eight, or ten cycles. Unlike current suprasystolic techniques, such cardiac cycle data may be available upon reaching the target pressure. This availability can reduce the need to ignore or discount one or more of the first several cardiac cycles from any suprasystolic measurement. Cuff compression using current techniques can cause conscious or unconscious muscle movement, affecting signals obtained during the first few beats at a suprasystolic pressure. Such data may be unsuitable for parameter determination, thereby prolonging the static phase. A more gradual compression of a patient's limb or arteries up to a suprasystolic pressure can reduce or eliminate the effects of these unwanted movements.

As shown in FIG. 1, system 10 can optionally include a signal analysis module 22, a communication module 24, or an accelerometer 26. These components may operate with one or more of the components of system 10 as described above.

Signal analysis module 22 may be configured to analyze one or more signals using one or more processors. Such analysis may be based on the output signal of sensor 18. For example, signal analysis module 22 can include one or more filters configured to filter a signal associated with sensor 18 or cuff control module 20. Such filters can include band-pass, high-pass, or low-pass filters.

In some embodiments, signal analysis module 22 may determine a hemodynamic parameter. A hemodynamic parameter can include an indication of cardiac or vascular health, such as, for example, an indication of cardiac, circulatory, or vascular functionality. Specifically, a hemodynamic parameter can include a heart rate, a blood pressure, a vessel compliance, an aortic index, an augmentation index, reflected wave ratio, or an indication of treatment. Blood pressure can include systolic, diastolic, or mean atrial pressure. An indication of treatment can include a parameter reflecting the affect of a drug treatment, or one or more treatments of a disease state.

In some embodiments, a hemodynamic parameter can be determined based on a suprasystolic measurement. In other embodiments, a hemodynamic parameter can be determined based on a first set of data obtained during inflation of cuff 12 and a second set of data obtained during general maintenance of cuff 12 at about the target pressure, as explained below in detail. The first or second sets of data can include various data associated with a signal waveform associated with patient 14 and/or cuff 12, and may include amplitude, frequency, morphology, feature, or mathematically derived data. Data can be derived from a derivative, integration, or frequency analysis, such as, for example, a fast-Fourier transform. Data may also be derived from various algorithms, including curve fitting, neural network, filtering, smoothing, or data processing.

System 10 can further include an accelerometer 26 to detect movement. Accelerometer 26 can be configured to detect movement in one, two, or three dimensions. For example, accelerometer 26 could be used to detect movement of patient 14 or movement of the arm of patient 14.

A signal arising from accelerometer 26 could be used to provide additional information to another module. For example, if movement of patient 14 is sufficient to interfere with sensor 18, a signal from accelerometer 26 may be transmitted to cuff control module 20 to halt the pressure cycle. In-addition, a signal from accelerometer 26 may be transmitted to signal analysis module 22 to cancel or reset a calculation. Data obtained from sensor 18 could be combined with data from accelerometer 26 to determine if an irregular signal may be caused by a motion artifact. Various data from accelerometer 26 may be processed to provide additional data to determine one or more hemodynamic parameters.

System 10 can further include a communication module 24 configured to provide communication to patient 14 or one or more operators. For example, communication module 24 could include a display configured to display one or more hemodynamic parameters. In other embodiments, communication module could include a transmitter configured to transmit data to a remote location. Communication module 24 may further include audio output to communicate with patient 14 and/or an operator of system 10.

In addition to the components outlined above, system 10 may include various other components as required, such as, for example, a memory, a power source, and a user input. One or more components described herein may be combined or may be separate and operate with wireless or wired communication links. Moreover, the various components of system 10 could be integrated into a single processing unit or may operate as separate processors. In operation, one or more processors can be configured to operate in conjunction with one or more software programs to provide the functionality of system 10.

Figure 2:
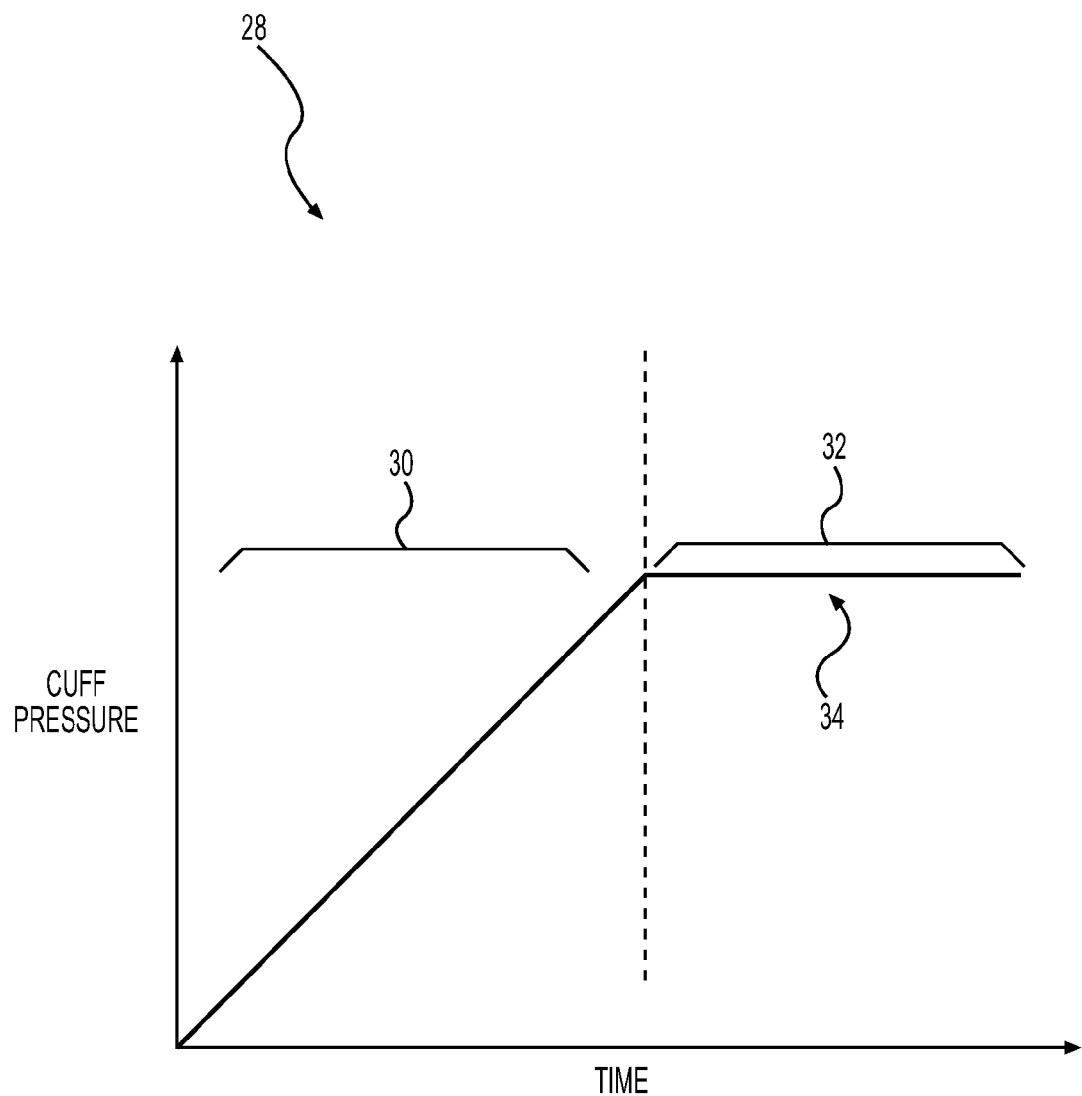
FIG. 2 illustrates a pressure pulse applied by the monitoring system, according to an exemplary embodiment.

FIG. 2 shows a cuff pressure waveform 28 as applied to a patient over a period of time, according to an exemplary embodiment. For example, waveform 28 may be applied to patient 14 using system 10 as indicated in FIG. 1. In some embodiments, waveform 28 can include a dynamic phase 30 and a static phase 32.

Dynamic phase 30 can include a generally increasing pressure. For example, as indicated in FIG. 2, dynamic phase 30 can include a continuously increasing linear pressure curve. In other embodiments, dynamic phase 30 can include a step wise pressure increase, a curved pressure increase, an exponential pressure increase, a gradual, or a rapid pressure increase.

During dynamic phase 30, one or more sets of data may be obtained using one or more sensors. Such data may be analyzed, as described in detail below, to determine a target pressure 34. Target pressure 34 can be greater than systolic pressure or about equal to systolic pressure. In some embodiments, target pressure 34 can be about equal to a suprasystolic pressure.

Static phase 32 can include generally maintaining a cuff pressure at about target pressure 34. In operation, a target pressure can be determined during dynamic phase 30 and applied during static phase 32. Target pressure 34 can include a generally constant pressure. In some embodiments, target pressure 34 can fluctuate within a range of values. For example, target pressure 34 can include values within about ±2%, ±5%, ±10%, or ±20%.

In order to reduce patient discomfort, the duration of dynamic phase 30 and static phase 32 should be less than about 60 seconds. In some embodiments, the duration of phases 30, 32 can be less than about 45 seconds. In some embodiments, the duration of phases—; ~3.0, 32 can be less than about 30 seconds. In particular, the duration of dynamic phase 30 can be less than about 15 seconds and the duration of static phase 32 can be less than about 10 seconds. Although FIG. 2 shows dynamic phase 20 and static phase 32 juxtaposed, in some embodiments these phases may be separated by one or more other phase of differing cuff pressure and/or duration.

Figure 3:
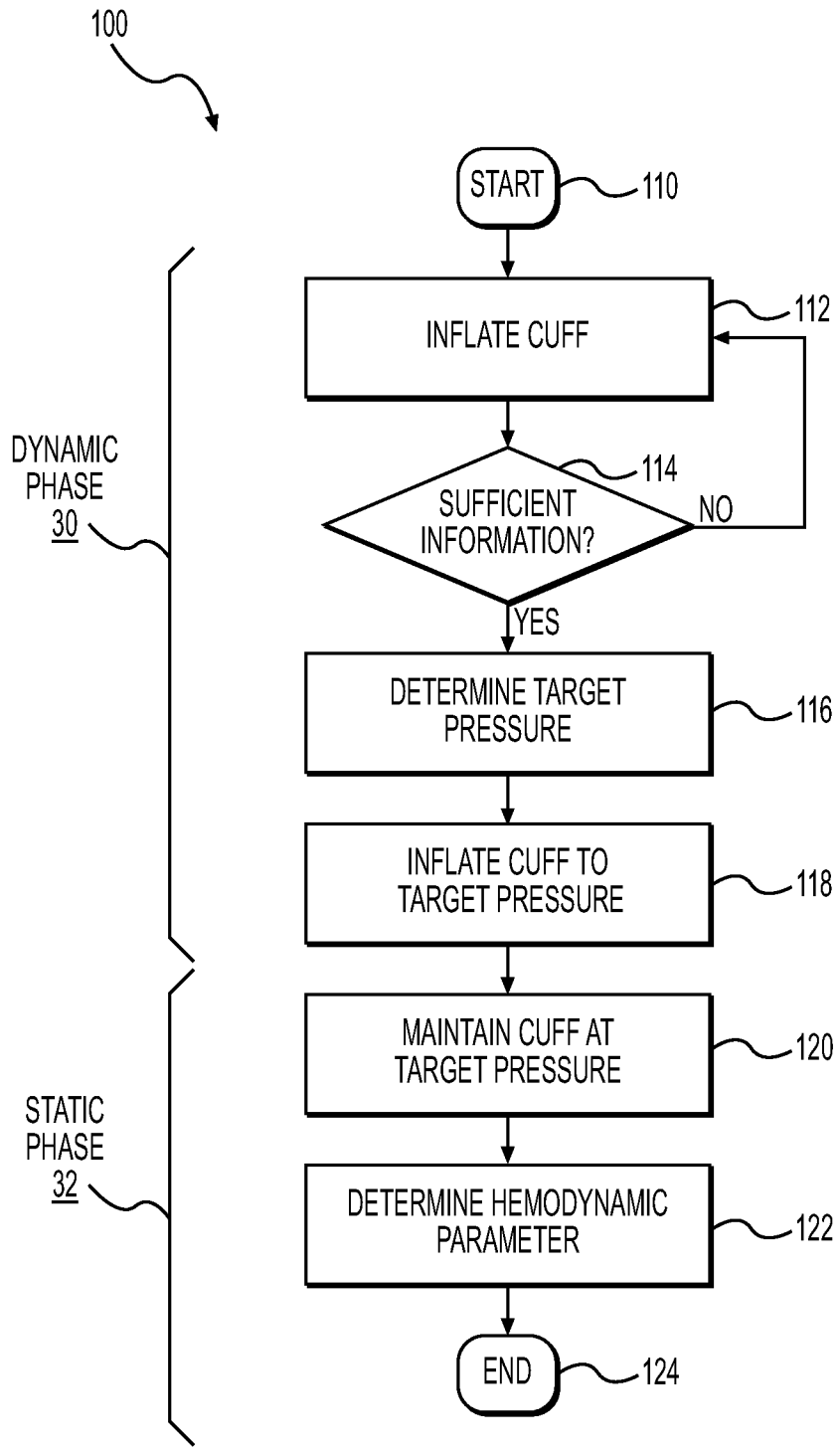
FIG. 3 illustrates a first flow chart, according to an exemplary embodiment.
Figure 4:
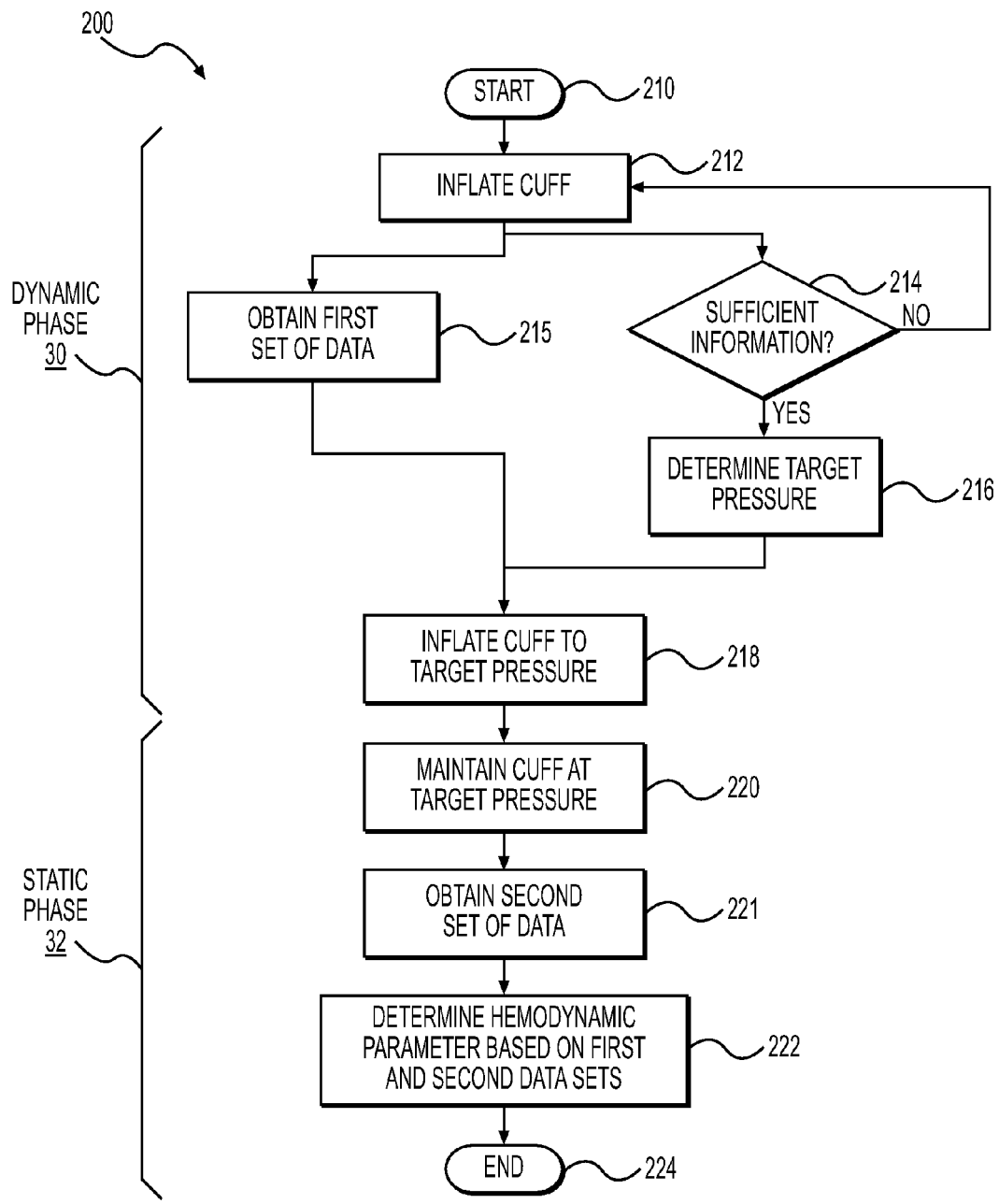
FIG. 4 illustrates a second flow chart, according to another exemplary embodiment.

FIGS. 3 and 4 illustrate flow charts of two exemplary embodiments according to the present disclosure. As described above with regard to FIG. 1, various modules can include one or more hardware components and one or more software components that operate to control an operation of system 10. Each step described below can be understood as corresponding to one or more computational instructions. These computational instructions can operate based on hardware and/or software components of system 10, and may operate on one or more processors.

FIG. 3 includes a process 100 according to an exemplary embodiment of the present disclosure. Step 110, labeled "Start," may include one of more steps required to initiate an operation of system 10. For example, system 10 may be turned on, a calibration protocol may be started, a cuff may be placed about a patient's arm, an operator may enter information to identify a patient, or information could be extracted from a database. Further, various components of system 10 may be calibrated or tested to ensure proper functioning. These operations could include a check of cuff integrity, if sufficient power is available, a calibration of one or more sensors, or confirmation of proper processor functioning. Also, other information may be entered into system 10, such as a patient identification, weight, gender, height, or other suitable data.

After system 10 has completed start 110, cuff 12 may be inflated (Step 112). This step may be considered the start of dynamic phase 30. In some embodiments, Step 112 could be initiated as part of Step 110.

As described above with regard to FIG. 1, cuff controller 16 may operate to inflate cuff 12. During inflation, sensor 18 may detect one or more signals. These signals may be analyzed by cuff control module 20 to determine if sufficient information has been obtained (Step 114). Sufficient information can refer to providing one or more algorithms with information sufficient to determine when cuff inflation should be terminated. For example, an algorithm could determine a target pressure for cuff inflation. In other embodiments, an algorithm could determine a time to stop cuff inflation.

In one embodiment, an algorithm may use oscillometric pulse data obtained during dynamic phase 30. The data may be analyzed in real time until such a point that an algorithm deems the data sufficient for a reading determination. Such data can relate to the maturity of the pulse envelope or the amount of envelope found during inflation. The collected pulse data can be filtered and/or conditioned. In other embodiments, a model curve can be fit to the data. In yet other embodiments, data can be submitted to a trained network of mathematical routines. Such analysis can be used to determine a systolic pressure or a diastolic pressure.

For example, the SureBP algorithm could be used to determine a systolic pressure. Such an algorithm is described in "Clinical evaluation of the Welch Allyn SureBP algorithm for automated blood pressure measurement," by Bruce Alpert, which is hereby incorporated by reference in its entirety. Such an algorithm can provide an accurate measure of systolic pressure during inflation, whereby the mean error is less than about 1 mmHg and the standard deviation of the mean error is less than about ±7 mmHg. In other embodiments, such an algorithm could provide a mean error of less than about 5 mmHg and a standard deviation of less than about ±5 mmHg.

If an algorithm determines that sufficient information has not yet been obtained, cuff inflation (Step 112) can continue until sufficient information has been obtained. One or more safety algorithms could also be used to limit cuff inflation to a maximum pressure. For example, process 100 may terminate if cuff pressure reaches about 200 mmHg.

After sufficient information has been obtained for an algorithm to determine a suitable stopping point for cuff inflation, a target pressure may be determined (Step 116). In some embodiments, the target pressure may include determining a systolic pressure. A suprasystolic pressure may then be determined based on the systolic pressure. For example, a suprasystolic pressure may be determined by adding about 10-40 mmHg to the value of the systolic pressure. The value of the target pressure may be determined based on the suprasystolic pressure. In some embodiments, the target pressure may be set to the same value as the suprasystolic pressure.

Once a target pressure has been determined (Step 116), cuff inflation may be continued to the target pressure (Step 118). Once cuff inflation reaches the target pressure, dynamic phase 30 can be considered complete and static phase 32 may begin. During static phase 32, cuff pressure can be maintained generally about the target pressure (Step 120). As previously described, such maintenance can include minor fluctuations about the target pressure.

During static phase 32, one or more hemodynamic parameters may be determined (Step 122). The hemodynamic parameters may be determined using suprasystolic analysis methods. For example, as described in U.S. Pat. No. 6,994,675 to Sharrock, large arterial vascular compliance may be determined using one of more signals obtained during static phase 32 (i.e. a suprasystolic phase). While Sharrock describes the use of a wideband acoustic transducer, signals from other pressure transducers can be used to analyze temporal or amplitude variations of signals obtained during the suprasystolic phase. U.S. Patent Application Publication No. 2006/0224070 to Sharrock et al. describes using suprasystolic measurements to determine Augmentation index, cardiac performance and cardiac stroke volume. U.S. Patent Application Publication No. 2009/0012411 to Lowe et al. describes using oscillometric techniques to analysis suprasystolic signals. Each of these references is hereby incorporated by reference in their entirety.

Following Step 122, process 100 may end (Step 124). Termination of process 100 can include gradual or rapid cuff deflation, display of one or more hemodynamic parameters, or power shut-down.

FIG. 4 includes a process 200 according to another exemplary embodiment of the present disclosure. Process 200 can include various steps similar to the steps described above for process 100. For example, Step 210, labeled "Start," may include one of more steps required to initiate an operation of system 10, as previously described for Step 110. Similarly, Steps 212, 214, 216, and 218 can occur during dynamic phase 30, as described above for Steps 112, 114, 116, and 118, respectively. Further, Steps 220 and 224 can occur during static phase 32, as described above for Steps 120 and 124, respectively.

Process 200 can include one or more additional steps during dynamic phase 30. In some embodiments, a first set of data can be obtained during dynamic phase 30 (Step 215). Such data can include information obtained from an oscillometric pulse. In some embodiments, the source of the first set of data may be different to the source providing data to determine the target pressure.

Process 200 can also include one or more additional steps during static phase 32. In some embodiments, a second set of data can be obtained during static phase 32 (Step 221). As described above, first and second sets of data can include any signal waveform data associated with patient 14 and/or cuff 12, and may include amplitude, frequency, morphology, feature, or mathematically derived data.

Based on first and second data sets, a hemodynamic parameter can be determined (Step 222). First and second data sets can be obtained and compared and contrasted to determine one or more parameters. For example, a beat-to-beat time during dynamic phase 30 can be compared to a beat-to-beat time during static phase 32. Such a comparison can be used to check for irregular heart beat timing. Other parameters can be determined based on comparing unloaded (i.e. dynamic phase 30) data with loaded (i.e. static phase 32) data. These two separate sample conditions can also be contrasted to determine one or more parameters using other methods known in the art.

In addition, analysis techniques can be used to reduce signal noise. For, example, first and second data sets may be used to remove common noise associated with both sets of data. A cleaner signal may be used to more accurately or precisely determine a hemodynamic parameter.

In other embodiments, one or more parameters determined during static phase 32 could be used to confirm any determinations based on data obtained during dynamic phase 30. For example, a second determination of systolic pressure could be made based on a second set of data obtained during static phase 32. The two values of systolic pressure could be compared to ensure that both are within acceptable limits to confirm the accuracy of any calculated parameters. If outside acceptable limits, process 200 may be terminated (Step 224) and repeated if desired.

Other embodiments of the present disclosure will be apparent to those skilled in the art from consideration of the specification and practice of the disclosure contained herein. It is intended that the specification and examples be considered as exemplary only, with a true scope and spirit of the present disclosure being indicated by the following claims.

What is claimed is:

1. A method of manufacturing a measurement system, comprising:
    providing a cuff;
    providing a cuff controller to inflate the cuff to at least partially occlude an artery of a patient during a single dynamic phase;
    configuring the cuff controller to maintain inflation of the cuff about a target pressure during a static phase, wherein the target pressure is a suprasystolic pressure;
    providing a first sensor to acquire a signal associated with the at least partially occluded artery; and
    providing a signal analysis module configured to determine a parameter based on the signal from the first sensor, wherein the parameter is determined based on a first set of data obtained over more than two cardiac cycles during the single dynamic phase and a second set of data obtained during the static phase, the second set of data being obtained over a defined number of cardiac cycles immediately following the beginning of the static phase.

2. The method of claim 1, wherein the signal analysis module determines during inflation whether a suprasystolic measurement should be performed.

3. The method of claim 2, wherein the determination of whether a suprasystolic measurement should be performed is at least partially based on a physiological indicator.

4. The method of claim 1, wherein the signal analysis module determines irregular heart beat timing using the first and second sets of data.

5. The method of claim 4, wherein the first set of data includes a first beat-to-beat time and the second set of data includes a second beat-to-beat time.

6. The method of claim 1, further comprising providing a second sensor.

7. The method of claim 6, wherein an irregular signal is determined using data from the second sensor and the signal, wherein the second sensor is an accelerometer.

8. The method of claim 1, further comprising providing a filter to filter the signal.

9. The method of claim 1, wherein the parameter is used to provide an indication of at least one of cardiac health, vascular health, and drug treatment.

10. A method of determining a parameter of a patient, comprising:
    inflating a cuff to at least partially occlude an artery of the patient during a single dynamic phase;
    substantially maintaining inflation of the cuff about a target pressure during a static phase, wherein the target pressure is a suprasystolic pressure;
    acquiring a signal associated with the at least partially occluded artery using a first sensor; and
    determining both a systolic pressure and the target pressure during the single dynamic phase and based on the signal, and control the cuff during the dynamic phase and the static phase; and
    determining a parameter, using a signal analysis module, based on the signal, wherein the parameter is determined based on a first set of data obtained over more than two cardiac cycles during the single dynamic phase and a second set of data obtained during the static phase, the second set of data being obtained over a defined number of cardiac cycles immediately following the beginning of the static phase.

11. The method of claim 10, further comprising determining during inflation using the signal analysis module whether a suprasystolic measurement should be performed.

12. The method of claim 11, wherein the determination of whether a suprasystolic measurement should be performed is at least partially based on a physiological indicator.

13. The method of claim 10, further comprising determining an irregular heart beat timing using the first and second sets of data.

14. The method of claim 13, wherein the first set of data includes a first beat-to-beat time and the second set of data includes a second beat-to-beat time.

15. The method of claim 10, further comprising maintaining the target pressure for less than about 10 seconds.

16. The method of claim 10, further comprising determining an irregular signal using the signal analysis module.

17. The method of claim 16, wherein the irregular signal is determined using data acquired from a second sensor, wherein the second sensor is an accelerometer, and the signal from the first sensor.

18. The method of claim 10, wherein the signal analysis module uses a filter to filter the signal acquired using the first sensor.

19. The method of claim 10, wherein the parameter is used to provide an indication of at least one of cardiac health, vascular health, and drug treatment.

20. A system for monitoring a patient, comprising:
    a cuff configured to inflate to at least partially occlude an artery of the patient;
    a cuff controller configured to inflate the cuff to a target pressure during a dynamic phase and, following the dynamic phase, generally maintain inflation of the cuff at about the target pressure during a static phase;
    a sensor configured to receive a signal associated with the at least partially occluded artery;
    a cuff control module configured to determine both a systolic pressure and the target pressure in real time during the dynamic phase and based on the output signal, and control the cuff controller during the dynamic phase and the static phase; and
    a signal analysis module configured to determine an indication for the patient based on the signal, wherein the indication is determined based on a first set of data obtained over more than two cardiac cycles during the dynamic phase and a second set of data obtained over a defined number of cardiac cycles during the static phase.

21. The system of claim 20, wherein the indication is of at least one of cardiac health, vascular health, and drug treatment.

\* \* \* \* \*